(12) United States Patent
Callot et al.

(10) Patent No.: US 12,275,808 B2
(45) Date of Patent: Apr. 15, 2025

(54) METHOD FOR PRODUCING SUPERABSORBENT PARTICLES

(71) Applicant: BASF SE, Ludwigshafen (DE)

(72) Inventors: Rene Callot, Antwerp (BE); Karl Possemiers, Antwerp (BE); Ruediger Funk, Ludwigshafen (DE); Marco Krueger, Ludwigshafen (DE); Matthias Weismantel, Ludwigshafen (DE); Juergen Schroeder, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 849 days.

(21) Appl. No.: 17/422,466

(22) PCT Filed: Jan. 13, 2020

(86) PCT No.: PCT/EP2020/050632
§ 371 (c)(1),
(2) Date: Jul. 13, 2021

(87) PCT Pub. No.: WO2020/151975
PCT Pub. Date: Jul. 30, 2020

(65) Prior Publication Data
US 2022/0089789 A1    Mar. 24, 2022

(30) Foreign Application Priority Data
Jan. 23, 2019  (EP) ..................... 19153264

(51) Int. Cl.
*C08F 2/18* (2006.01)
*A61F 13/53* (2006.01)
(Continued)

(52) U.S. Cl.
CPC ............... *C08F 2/18* (2013.01); *A61F 13/53* (2013.01); *B01J 20/267* (2013.01); *B01J 20/285* (2013.01);
(Continued)

(58) Field of Classification Search
CPC ........ F26B 17/023; F26B 17/04; A61F 13/53; A61F 2013/530481; B01J 20/285;
(Continued)

(56) References Cited

U.S. PATENT DOCUMENTS 2,921,006 A * 1/1960 Schmitz ............... C08F 2/46
  976/DIG. 444
2001/0007274 A1* 7/2001 Sanada ................ C08F 8/42
  156/329

FOREIGN PATENT DOCUMENTS

DE   2162229 A1   6/1973
DE   19529925 A1  2/1997
(Continued)

OTHER PUBLICATIONS

International Application No. PCT/EP2020/050632, International Search Report, mailed May 29, 2020.
(Continued)

*Primary Examiner* — Brian A Mccaig
(74) *Attorney, Agent, or Firm* — Element IP, PLC

(57) ABSTRACT

A process for producing superabsorbent particles by polymerizing a monomer solution or suspension, comprising drying of the resultant aqueous polymer gel in an air circulation belt dryer, grinding, classifying, and optionally thermal surface postcrosslinking, wherein the aqueous polymer gel is introduced into the air circulation belt dryer by means of an oscillating conveyor belt and that guide devices are located at the edges of the conveyor belt.

14 Claims, 1 Drawing Sheet

(51) Int. Cl.
*B01J 20/26* (2006.01)
*B01J 20/285* (2006.01)
*C08F 2/04* (2006.01)
*C08F 6/00* (2006.01)
*C08F 20/04* (2006.01)
*F26B 17/02* (2006.01)
*F26B 17/04* (2006.01)

(52) U.S. Cl.
CPC ............... *C08F 2/04* (2013.01); *C08F 6/008* (2013.01); *C08F 20/04* (2013.01); *F26B 17/023* (2013.01); *F26B 17/04* (2013.01); *A61F 2013/530481* (2013.01); *B01J 2220/68* (2013.01)

(58) Field of Classification Search
CPC ...... B01J 2220/68; C08J 3/24; C08J 2333/02; B08B 1/165; C08F 2/04; C08F 2/16; C08F 2/18; C08F 4/40; C08F 6/008
See application file for complete search history.

(56) References Cited

FOREIGN PATENT DOCUMENTS

| | | |
|---|---|---|
| EP | 2700667 A1 | 2/2014 |
| GB | 1412116 A | 10/1975 |
| JP | 2005-225587 A | 8/2005 |
| JP | 2016-078959 A | 5/2016 |
| WO | WO-2008/087114 A1 | 7/2008 |
| WO | WO-2010/139680 A2 | 12/2010 |
| WO | WO-2015/074966 A1 | 5/2015 |
| WO | WO-2020/064411 A1 | 4/2020 |

OTHER PUBLICATIONS

Graham, et al., "Chapter 3: Commercial Processes for the Manufacture of Superabsorbent Polymers", Modern Superabsorbent Polymer Technology, ed. Buchholz, et al., 2nd Edition, 1998, pp. 69-117.

* cited by examiner

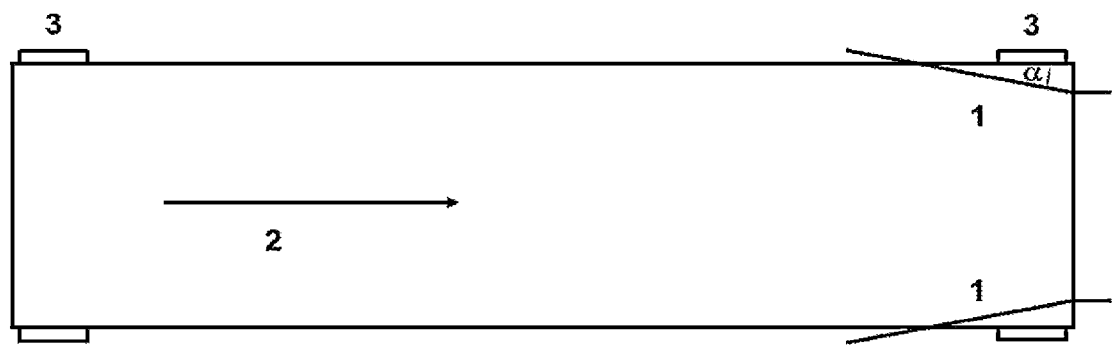

METHOD FOR PRODUCING SUPERABSORBENT PARTICLES

CROSS-REFERENCE TO RELATED APPLICATIONS

This is the U.S. national phase of International Application No. PCT/EP2020/050632, filed Jan. 13, 2020, which claims the benefit of European Patent Application No. 19153264.7, filed on Jan. 23, 2019.

The present invention relates to a process for producing superabsorbent particles by polymerizing a monomer solution or suspension, comprising drying of the resultant aqueous polymer gel in an air circulation belt dryer, grinding, classifying, and optionally thermal surface postcrosslinking, wherein the aqueous polymer gel is introduced into the air circulation belt dryer by means of an oscillating conveyor belt and that guide devices are located at the edges of the conveyor belt.

Superabsorbents are used to produce diapers, tampons, sanitary napkins and other hygiene articles, but also as water-retaining agents in market gardening. Superabsorbents are also referred to as water-absorbing polymers.

The production of superabsorbents is described in the monograph "Modern Superabsorbent Polymer Technology", F. L. Buchholz and A. T. Graham, Wiley-VCH, 1998, pages 71 to 103.

To improve the performance properties, for example gel bed permeability (GBP) and absorption under a pressure of 49.2 g/cm² (AUL0.7 psi), superabsorbent particles are generally surface postcrosslinked. This increases the level of crosslinking of the particle surface, which can at least partly decouple the absorption under a pressure of 49.2 g/cm² (AUL0.7 psi) and the centrifuge retention capacity (CRC). This surface postcrosslinking can be performed in the aqueous gel phase. Preferably, however, dried, ground and sieved polymer particles (base polymer) are surface coated with a surface postcrosslinker and thermally surface postcrosslinked. Crosslinkers suitable for that purpose are compounds which can form covalent bonds to at least two carboxylate groups of the polymer particles.

WO 2008/087114 A1, WO 2010/139680 A2 and EP 2 700 667 A1 describe the loading of the transport belts of air circulation belt dryers with aqueous polymer gel by means of oscillating conveyor belts.

It was an object of the present invention to provide an improved process for producing superabsorbents, especially a more stable operation of the oscillating conveyor belt used.

The object was achieved by a process for producing superabsorbents by polymerizing a monomer solution or suspension comprising
a) at least one ethylenically unsaturated monomer which bears acid groups and is at least partly neutralized,
b) at least one crosslinker and
c) at least one initiator, comprising drying of the resultant aqueous polymer gel in an air circulation belt dryer, grinding, classifying, and optionally thermal surface postcrosslinking, wherein the aqueous polymer gel is introduced into the air circulation belt dryer by means of an oscillating conveyor belt and guide devices (1) are located at the edges of the conveyor belt (2).

An oscillating conveyor belt is a conveyor belt pivotable periodically at a vertical axis. The conveyor belt of the oscillating conveyor belt itself runs essentially at constant speed. The conveyor belt of the oscillating conveyor belt has a distinctly smaller width than the conveyor belt of the air circulation belt dryer. The periodic pivoting motion of the oscillating conveyor belt results in homogeneous coverage of the conveyor belt of the air circulation belt dryer with polymer gel over the total width.

FIG. 1 shows an embodiment of the present invention with guide devices (1), conveyor belt (2), and drive/deflection drum (3).

In one preferred embodiment of the present invention, the guide devices (1) are located on the discharge end of the conveyor belt, with the length of the guide devices (1) being preferably from 5% to 70%, more preferably from 10% to 50%, very preferably from 15% to 30% of the length of the conveyor belt, and the length of the conveyor belt being the distance of the pivot axis from the discharge end.

The height of the guide devices (1) is preferably from 5 to 30 cm, more preferably from 8 to 25 cm, very preferably from 10 to 20 cm.

The length and the height of the guide devices (1) are, for example, 5% to 70% and 5 to 30 cm, 5% to 70% and 8 to 25 cm, 5% to 70% and 10 to 20 cm, 10% to 50% and 5 to 30 cm, 10% to 50% and 8 to 25 cm, 10% to 50% and 10 to 20 cm, 15% to 30% and 5 to 30 cm, 15% to 30% and 8 to 25 cm or 15% to 30% and 10 to 20 cm.

The guide devices (1) may be rotated about the angle α at right angles to the running direction of the conveyor belt, to the middle of the conveyor belt in running direction, the guide devices (1) being rotated preferably by 3° to 15°, more preferably by 6° to 12°, very preferably by 8° to 10°.

The part of the guide devices (1) that is in contact with the conveyor belt ought not to be too hard. Suitable materials are natural or synthetic rubbers, such as silicone rubber, polyetheretherketone (PEEK), halogenated polyolefins, such as polyvinyl chloride (PVC) or polytetrafluoroethylene (PTFE), polyamide (PA), polypropylene (PP) or polyethylene (PE). Silicone rubber is preferred.

The guide devices (1) preferably follow the curvature of the conveyor belt. The preferred guide devices are at as small a distance as possible to the conveyor belt. If the distance is too great, polymer gel passes to the outside, between guide device (1) and conveyor belt. Too low a distance causes friction, i.e. unwanted mechanical loading, between guide device (1) and conveyor belt.

If the material of the guide devices (1) that is in contact with the conveyor belt is sufficiently flexible, the guide devices (1) may even lie directly on the conveyor belt. It is possible, in fact, for the flexible material of the guide devices (1) that lies on the conveyor belt, silicone rubber for example, to be bent inward, i.e. toward the transported polymer gel.

The guide devices (1) preferably project beyond the discharge end of the conveyor belt. The preferred guide devices (1) here follow the curvature at the deflection drum (3) downward. The regions of the guide devices (1) which protrude beyond the discharge end of the conveyor belt are preferably parallel to the running direction of the conveyor belt.

The present invention is based on the finding that polymer gel can get under the conveyor belt. This polymer gel then gets onto the drum surfaces of the drive drum or the deflection drum. The polymer gel leads to belt misalignment on the drum surfaces, meaning that the circulating conveyor belt on the drum moves to the side. Moreover, the polymer gel on the surface of the drive drum leads to slippage of the drum, i.e. to a reduction in drive power. The guide devices (1) prevent polymer gel from getting under the conveyor belt. Belt misalignment and slippage of the drive drum are thus prevented.

In one preferred embodiment of the present invention, the bottom face of the returning conveyor belt is additionally cleaned of adhering polymer gel by means of at least one stripping device.

The bottom face of the returning conveyor belt is the outside of the conveyor belt, which after turnaround receives a further metered amount of polymer gel. The top face of the returning conveyor belt is the inside of the conveyor belt, which is not to come into contact with polymer gel.

The distance of the stripping device from the discharge end of the conveyor belt is preferably less than 20% of the length of the conveyor belt, more preferably less than 10% of the length of the conveyor belt, very preferably less than 5% of the length of the conveyor belt, the length of the conveyor belt being the distance of the pivot axis from the discharge end.

The stripping device is not subject to any restrictions. Brushes arranged transversely to the running direction are suitable, for example. Another possibility is the use of a scraper. A scraper is a stripping device which is arranged transversely to the conveying direction and which is made of a non-flexible material. An example of a suitable non-flexible material is polytetrafluoroethylene. In order to prevent damage to the conveyor belt, the scraper ought to have very little direct contact, or none, with the conveyor belt.

The scraper ought to be inclined relative to the running direction of the returning conveyor belt. This promotes the peeling-off of the adhering polymer gel and prevents a jam between conveyor belt and scraper. The polymer gel that is stripped off typically falls onto the conveyor belt of the air circulation belt dryer.

The scraper is preferably at an inclination of 5° to 45°, more preferably of 10° to 35°, very preferably of 15° to 25° relative to the perpendicular against the running direction of the conveyor belt. The distance of the scraper to the underside of the returning conveyor belt is preferably 0.1 to 5 mm, more preferably 0.2 to 2 mm, very preferably 0.5 to 1.5 mm.

The conveyor belt has a length of preferably 2 to 10 m, more preferably from 2.5 to 8 m, most preferably from 3 to 6 m, the length of the conveyor belt being the distance of the pivot axis from the discharge end.

The conveyor belt has a width of preferably 0.5 to 1.5 m, more preferably of 0.6 to 1.2 m, most preferably of 0.7 to 0.9 m.

The conveyor belt speed is preferably from 0.2 to 2.0 m/s, more preferably from 0.3 to 1.5 m/s, most preferably from 0.4 to 1.0 m/s.

It is possible to use the conveyor belts that are customary for this purpose. The surface of the conveyor belts, i.e. the side that comes into contact with the polymer gel, should be water repellent and have a water contact angle at 23° C. of preferably at least 60°, more preferably at least 80°, most preferably at least 100°. The contact angle is a measure of the wetting behavior and is measured to DIN 53900.

The water content of the polymer gel on the conveyor belt is preferably from 20 to 80% by weight, more preferably from 30 to 70% by weight, most preferably from 40 to 60% by weight.

The temperature of the polymer gel on the conveyor belt is preferably from 60 to 105° C., more preferably from 70 to 100° C. and most preferably from 80 to 95° C.

The production of the superabsorbents is described in detail hereinafter:

The superabsorbents are produced by polymerizing a monomer solution or suspension, and are typically water-insoluble.

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

The monomers a) typically comprise polymerization inhibitors, preferably hydroquinone monoethers, as storage stabilizers.

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 02/032962 A2.

The amount of crosslinker b) is preferably 0.05% to 1.5% by weight, more preferably 0.1% to 1% by weight and most preferably 0.3% to 0.6% by weight, calculated in each case on the basis of the total amount of monomer a) used. With rising crosslinker content, the centrifuge retention capacity (CRC) falls and the absorption under a pressure of 21.0 g/cm$^2$ (AUL0.3 psi) passes through a maximum.

Initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is preferably the disodium salt of 2-hydroxy-2-sulfonatoacetic acid or a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Typically, an aqueous monomer solution is used. The water content of the monomer solution is preferably from 40% to 75% by weight, more preferably from 45% to 70% by weight and most preferably from 50% to 65% by weight. It is also possible to use monomer suspensions, i.e. monomer solutions with solubility-exceeding monomer a), for example sodium acrylate. As the water content rises, the energy expenditure in the subsequent drying rises and, as the water content falls, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors for the polymerization are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel which has to be comminuted, for example in an extruder or kneader.

To improve the drying properties, the comminuted polymer gel obtained by means of a kneader can additionally be extruded.

The acid groups of the resulting polymer gels have typically been partly neutralized. Neutralization is preferably carried out at the monomer stage. This is typically accomplished by mixing in the neutralizing agent as an aqueous solution or else preferably as a solid. The degree of neutralization is preferably from 40 to 85 mol %, more preferably from 50 to 80 mol % and most preferably from 60 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof. Solid carbonates and hydrogencarbonates can also be introduced here in encapsulated form, preferably into the monomer solution directly prior to the polymerization, into the polymer gel during or after the polymerization and prior to the drying thereof. The encapsulation is effected by coating of the surface with an insoluble or only gradually soluble material (for example by means of film-forming polymers, of inert inorganic materials or of fusible organic materials) which delays the dissolution and reaction of the solid carbonate or hydrogencarbonate to such a degree that carbon dioxide is not released until during the drying and the superabsorbent formed has high internal porosity.

The polymer gel is then typically dried with an air circulation belt dryer until the residual moisture content is preferably 0.5 to 10% by weight, more preferably 1 to 7% by weight and most preferably 2 to 5% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the polymer gel before the drying is preferably from 25% to 90% by weight, more preferably from 35% to 70% by weight, most preferably from 40% to 60% by weight. Subsequently, the dried polymer gel is crushed and optionally coarsely comminuted.

Thereafter, the dried polymer gel is typically ground and classified, and the apparatus used for grinding may typically be single or multistage roll mills, preferably two- or three-stage roll mills, pin mills, hammer mills or vibratory mills.

The average particle size of the polymer particles removed as the product fraction is preferably from 150 to 850 μm, more preferably from 250 to 600 μm, very particularly from 300 to 500 μm. The average particle size of the product fraction may be determined by means of EDANA recommended test method No. WSP 220.2 (05) "Particle Size Distribution", where the proportions by mass of the screen fractions are plotted in cumulated form and the average particle size is determined graphically. The average particle size here is the value of the mesh size which arises for a cumulative 50% by weight.

To further improve the properties, the polymer particles can be thermally surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

The amount of surface postcrosslinker is preferably 0.001% to 2% by weight, more preferably 0.02% to 1% by weight and most preferably 0.05% to 0.2% by weight, based in each case on the polymer particles.

In a preferred embodiment of the present invention, polyvalent cations are applied to the particle surface in addition to the surface postcrosslinkers.

The polyvalent cations usable in the process of the invention are, for example, divalent cations such as the cations of zinc, magnesium, calcium and strontium, trivalent cations such as the cations of aluminum, iron, chromium, rare earths and manganese, tetravalent cations such as the cations of titanium and zirconium. Possible counterions are chloride, bromide, hydroxide, sulfate, hydrogensulfate, carbonate, hydrogencarbonate, nitrate, phosphate, hydrogenphosphate, dihydrogenphosphate and carboxylate, such as acetate and lactate. Aluminum hydroxide, aluminum sulfate and aluminum lactate are preferred.

The amount of polyvalent cation used is, for example, 0.001% to 1.5% by weight, preferably 0.005% to 1% by weight and more preferably 0.02% to 0.8% by weight, based in each case on the polymer.

The surface postcrosslinking is typically performed in such a way that a solution of the surface postcrosslinker is sprayed onto the dried polymer particles. After the spray application, the polymer particles coated with surface postcrosslinker are surface postcrosslinked and dried, and the surface postcrosslinking reaction can take place both before and during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e.

horizontal mixers have a horizontally mounted mixing shaft and vertical mixers a vertically mounted mixing shaft. Suitable mixers are, for example, horizontal Pflugschar® plowshare mixers (Gebr. Lodige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

The surface postcrosslinking is preferably performed in contact dryers, more preferably shovel dryers, most preferably disk dryers. Suitable dryers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany), Holo-Flite® dryers (Metso Minerals Industries Inc.; Danville; USA) and Nara Paddle Dryer (NARA Machinery Europe; Frechen; Germany). Moreover, fluidized bed dryers may also be used.

The surface postcrosslinking can be effected in the mixer itself, by heating the jacket or blowing in warm air. Equally suitable is a downstream dryer, for example a shelf dryer, a rotary tube oven or a heatable screw. It is particularly advantageous to effect mixing and thermal surface postcrosslinking in a fluidized bed dryer.

Preferred reaction temperatures are in the range of 100 to 250° C., preferably 110 to 220° C., more preferably 120 to 210° C., most preferably 130 to 200° C. The preferred dwell time at this temperature is preferably at least 10 minutes, more preferably at least 20 minutes, most preferably at least 30 minutes, and typically at most 60 minutes.

Subsequently, the surface postcrosslinked polymer particles can be classified again, with excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures the polymer particles tend to form lumps, and at higher temperatures water already evaporates to a noticeable degree. The amount of water used for remoisturizing is preferably from 1% to 10% by weight, more preferably from 2% to 8% by weight and most preferably from 3% to 5% by weight. The remoisturizing increases the mechanical stability of the polymer particles and reduces their tendency to static charging. The remoisturizing is advantageously performed in a cooler after the thermal surface postcrosslinking.

Suitable coatings for improving the free swell rate and the gel bed permeability (GBP) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, precipitated silica, such as Sipernat® D17, and surfactants, such as Span® 20.

The present invention further provides hygiene articles comprising superabsorbents produced by the process of the invention.

Methods:

The standard test methods described hereinafter and designated "WSP" are described in: "Standard Test Methods for the Nonwovens Industry", 2005 edition, published jointly by the Worldwide Strategic Partners EDANA (Herrmann-Debrouxlaan 46, 1160 Oudergem, Belgium, www.edana.org) and INDA (1100 Crescent Green, Suite 115, Cary, North Carolina 27518, USA, www.inda.org). This publication is obtainable both from EDANA and from INDA.

The measurements should, unless stated otherwise, be conducted at an ambient temperature of 23±2° C. and a relative air humidity of 50±10%. The water-absorbing polymer particles are mixed thoroughly before the measurement.

Centrifuge Retention Capacity

The centrifuge retention capacity (CRC) is determined by EDANA recommended test method No. WSP 241.2 (05) "Fluid Retention Capacity in Saline, After Centrifugation".

Extractables

The content of extractables of the water-absorbing polymer particles is determined by EDANA recommended test method No. WSP 270.2 (05) "Extractable".

EXAMPLE

By continuously mixing deionized water, 50% by weight sodium hydroxide solution and acrylic acid, an acrylic acid/sodium acrylate solution was prepared such that the degree of neutralization corresponded to 71.3 mol %. The solids content of the monomer solution was 38.8% by weight.

The polyethylenically unsaturated crosslinker used was polyethylene glycol-400 diacrylate (diacrylate proceeding from a polyethylene glycol with a mean molar mass of 400 g/mol). The amount used was 2 kg of crosslinker per t of monomer solution.

To initiate the free-radical polymerization, per t of monomer solution, 1.03 kg of a 0.25% by weight aqueous hydrogen peroxide solution, 3.10 kg of a 15% by weight aqueous sodium peroxodisulfate solution and 1.05 kg of a 1% by weight aqueous ascorbic acid solution were used.

The throughput of the monomer solution was 20 t/h. The reaction solution had a feed temperature of 23.5° C.

The individual components were metered in the following amounts continuously into a List Contikneter continuous kneader reactor with a capacity of 6.3 m³ (LIST AG, Arisdorf, Switzerland):

| | |
|---|---|
| 20 t/h | of monomer solution |
| 40 kg/h | of polyethylene glycol-400 diacrylate |
| 82.6 kg/h | of hydrogen peroxide solution/ sodium peroxodisulfate solution |
| 21 kg/h | of ascorbic acid solution |

Between the addition point for the crosslinker and the addition sites for the initiators, the monomer solution was inertized with nitrogen.

After about 50% of the residence time there was an additional metered addition to the reactor of fines (1000 kg/h) which were obtained from the production process by grinding and sieving. The dwell time of the reaction mixture in the reactor was 15 minutes.

The aqueous polymer gel obtained was applied to the conveyor belt of an air circulation belt dryer by means of an oscillating conveyor belt.

The air circulation belt dryer had a length of 48 m. The conveyor belt of the air circulation belt dryer had an effective width of 4.4 m.

The oscillating conveyor belt had a length of 5 m. The conveyor belt had a width of 0.8 m and an effective width of 0.5 m. The angle of repose of the aqueous polymer gel on the conveyor belt was about 15°. The cross section of the polymer gel bed on the conveyor belt was about 0.04 m². The speed of the conveyor belt was 0.5 m/s.

Proceeding from one end position, the oscillating conveyor belt was accelerated through a first pivot angle $\beta_1$ of 13° to an angular speed of 33°/s, decelerated through a second pivot angle $\beta_2$ of 20° to an angular speed of 17°/s and decelerated through a third pivot angle $\beta_3$ to the other end position. The total pivot angle was 50°. A double pass (from the first end position to the other end position and back) lasted about 7 s. The circulating conveyor belt had a surface of polytetrafluoroethylene (PTFE).

The temperature of the aqueous polymer gel on the oscillating conveyor belt was 90° C.

Located at the discharge end of the conveyor belt, at each of the edges of the conveyor belt, was a guide device (1), as shown in FIG. 1. The guide devices (1) had a length of in each case about 1200 mm and protruded about 100 mm beyond the discharge end of the conveyor belt. The part of the guide devices (1) that was in contact with the conveyor belt was made of silicone rubber and had a thickness of about 5 mm. The guide devices (1) were each rotated by about 8.5° at right angles to the running direction of the conveyor belt, to the middle of the conveyor belt in the running direction. That part of the guide devices that extended over the discharge end of the conveyor belt was again parallel to the running direction of the conveyor belt. The guide devices (1) followed the curvature of the deflection roller (3) up to the perpendicular, from where they were extended straight downward for about 165 mm.

Located on the bottom face of the oscillating conveyor belt was a stripping device. The stripping device was an elongated scraper mounted transversely to the running direction of the returning conveyor belt. The scraper had an inclination of 20° against the running direction of the returning conveyor belt. The distance of the stripping device from the discharge end was about 5 cm, i.e. the stripping device was located in a region of the deflection roller. The distance of the stripping device to the returning conveyor belt was 1 mm. Aqueous polymer gel adhering on the outside of the returning conveyor belt is stripped off using the stripping device.

Operation of the circulating conveyor belt was trouble-free. The guide devices (1) prevented polymer gel falling onto the top face of the returning conveyor belt from passing as polymer gel between drum and conveyor belt.

On the air circulation belt dryer, an air/gas mixture flowed continuously around the aqueous polymer gel and dried it. The residence time in the air circulation belt dryer was 37 minutes.

The dried polymer gel was ground and sieved to a particle size fraction of 150 to 850 μm.

The resulting water-absorbing polymer particles had a centrifuge retention capacity (CRC) of 34.9 g/g and an extractables content of 8.5% by weight.

The invention claimed is:

1. A process for producing superabsorbent particles by polymerizing a monomer solution or suspension comprising a) at least one ethylenically unsaturated monomer which bears an acid group and is at least partly neutralized, b) at least one crosslinker and c) at least one initiator, comprising drying a resultant aqueous polymer gel in an air circulation belt dryer, grinding, classifying, and optionally thermal surface postcrosslinking, wherein the aqueous polymer gel is introduced into the air circulation belt dryer by an oscillating conveyor belt, and wherein guide devices (1) are located at edges of the conveyor belt (2), wherein the guide devices (1) are rotated about an angle α at right angles to a running direction of the conveyor belt to the middle of the conveyor belt in running direction.

2. The process according to claim 1, wherein the guide devices (1) are located at a discharge end of the conveyor belt and a length of the guide devices (1) is from 15% to 30% of the length of the conveyor belt, the length of the conveyor belt being a distance of a pivot axis from the discharge end, and/or wherein a height of the guide devices (1) is from 10 to 20 cm.

3. The process according to claim 2, wherein the bottom face of the returning conveyor belt is cleaned of adhering polymer gel by at least one stripping device.

4. The process according to claim 3, wherein a distance of the stripping device from the discharge end of the conveyor belt is less than 5% of the length of the conveyor belt, the length of the conveyor belt being the distance of the pivot axis from the discharge end.

5. The process according to claim 3, wherein the at least one stripping device mounted on the bottom face of the returning conveyor belt is a scraper.

6. The process according to claim 5, wherein the scraper is at an inclination of 15° to 25° relative to the perpendicular against the running direction of the conveyor belt.

7. The process according to claim 5, wherein a distance of the scraper to the underside of the returning conveyor belt is from 0.1 to 5 mm.

8. The process according to claim 2, wherein the conveyor belt has a length of 2 to 10 m, the length of the conveyor belt being the distance of the pivot axis from the discharge end.

9. The process according to claim 1, wherein the guide devices (1) are rotated by 8° to 10°.

10. The process according to claim 1, wherein a part of the guide devices (1) that is in contact with the conveyor belt is made of silicone rubber.

11. The process according to any of claim 1, wherein the guide devices (1) follow a curvature of the conveyor belt.

12. The process according to claim 1, wherein the surface of the conveyor belt has a water contact angle at 23° C. of at least 60°.

13. A process for producing superabsorbent particles by polymerizing a monomer solution or suspension comprising
a) at least one ethylenically unsaturated monomer which bears an acid group and is at least partly neutralized,
b) at least one crosslinker and
c) at least one initiator,
comprising drying a resultant aqueous polymer gel in an air circulation belt dryer, grinding, classifying, and optionally thermal surface postcrosslinking, wherein the aqueous polymer gel is introduced into the air circulation belt dryer by an oscillating conveyor belt, and wherein guide devices (1) are located at edges of the conveyor belt (2),
wherein the guide devices (1) follow a curvature of the conveyor belt.

14. A process for producing superabsorbent particles by polymerizing a monomer solution or suspension comprising a) at least one ethylenically unsaturated monomer which bears an acid group and is at least partly neutralized,
b) at least one crosslinker and
c) at least one initiator,
comprising drying a resultant aqueous polymer gel in an air circulation belt dryer, grinding, classifying, and optionally thermal surface postcrosslinking, wherein the aqueous polymer gel is introduced into the air circulation belt dryer by an oscillating conveyor belt, and wherein guide devices (1) are located at edges of the conveyor belt (2),
wherein the guide devices (1) follow a curvature of the conveyor belt, and
wherein the guide devices (1) protrude beyond the discharge end of the conveyor belt.

* * * * *